(12) United States Patent
Macnamara et al.

(10) Patent No.: US 8,591,713 B2
(45) Date of Patent: Nov. 26, 2013

(54) ELECTROPHORESIS CASSETTE

(75) Inventors: Kenneth G. Macnamara, Edinburgh (GB); Jim Elliott, Edinburgh (GB)

(73) Assignee: Agilent Technologies, Inc., Santa Clara, CA (US)

( * ) Notice: Subject to any disclaimer, the term of this patent is extended or adjusted under 35 U.S.C. 154(b) by 275 days.

(21) Appl. No.: 12/996,009

(22) PCT Filed: Jun. 5, 2009

(86) PCT No.: PCT/GB2009/001413
§ 371 (c)(1),
(2), (4) Date: Feb. 7, 2011

(87) PCT Pub. No.: WO2009/147407
PCT Pub. Date: Dec. 10, 2009

(65) Prior Publication Data
US 2011/0114493 A1    May 19, 2011

(30) Foreign Application Priority Data

Jun. 6, 2008 (GB) .................................. 0810445.7

(51) Int. Cl.
*G01N 27/453* (2006.01)

(52) U.S. Cl.
USPC ........................... 204/470; 204/469; 204/616

(58) Field of Classification Search
USPC .......... 204/456, 466, 469, 470, 606, 616–620
See application file for complete search history.

(56) References Cited

U.S. PATENT DOCUMENTS

| | | | |
|---|---|---|---|
| 5,149,416 A * | 9/1992 | Osterhoudt et al. | 204/456 |
| 5,159,049 A * | 10/1992 | Allen | 204/456 |
| 5,354,442 A | 10/1994 | Allen et al. | |
| 5,455,344 A | 10/1995 | Harper et al. | |
| 5,837,288 A * | 11/1998 | Sylvester et al. | 424/484 |
| 2006/0118418 A1 | 6/2006 | Sivaram et al. | |
| 2011/0031120 A1 | 2/2011 | Inche et al. | |

FOREIGN PATENT DOCUMENTS

| | | |
|---|---|---|
| EP | 0809103 | 11/1997 |
| EP | 1224927 | 7/2002 |
| WO | WO 94/23092 A | 10/1994 |
| WO | WO 96/34276 | 10/1996 |
| WO | WO 2005/010520 A | 2/2005 |
| WO | WO 2009/093054 A1 | 7/2009 |

OTHER PUBLICATIONS

Brown et al, "Mixed anionic detergent/aliphatic alcohol-polyacrylamide gel electrophoresis alters the separation of proteins relative to conventional sodium dodecyl sulfate-polyacrylamide gel electrophoresis", Analytical Biochemistry, vol. 174, No. 1, pp. 337-348, Oct. 1, 1988.

Rocheleau et al, "Formamide modified polyacrylamide gels for DNA sequencing by capillary gel electrophoresis", Electrophoresis, vol. 13, No. 8, pp. 484-486, 1992.

* cited by examiner

*Primary Examiner* — Alex Noguerola

(57) ABSTRACT

A pre-packaged electrophoresis cassette (1), the cassette (1) comprising a gel layer (2) and a buffer solution layer (3), the gel layer comprising a first polymer made from a monomer and a cross-linker, and being in contact with the buffer solution layer to form a gel-buffer interface (4) for receiving a sample which is to undergo electrophoresis. The gel and/or the buffer solution are such that absorption of water by the gel layer from the buffer solution layer is inhibited, thereby maintaining the performance capabilities of the electrophoresis cassette during storage.

25 Claims, 13 Drawing Sheets

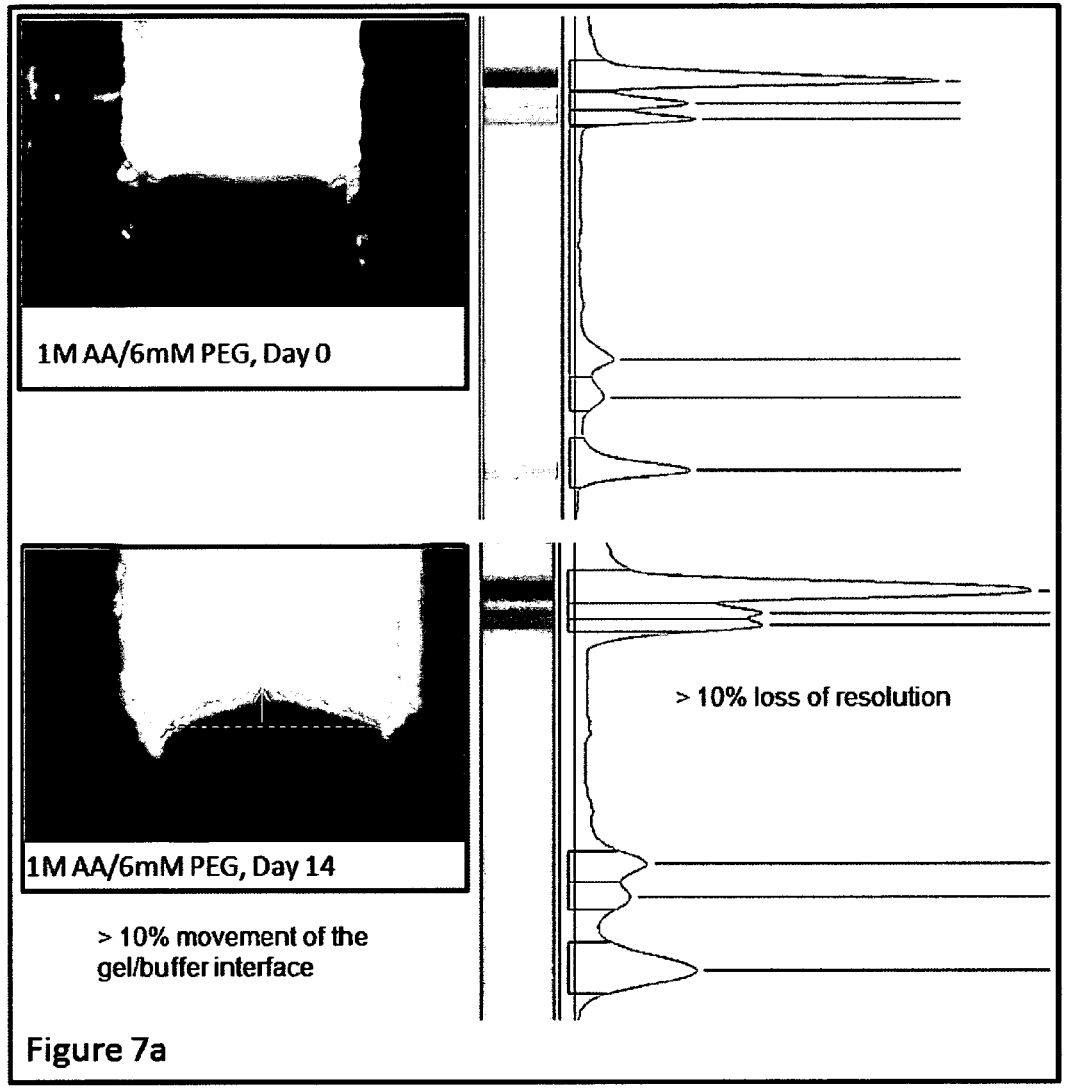

ELECTROPHORESIS CASSETTE

This application is the U.S. National Phase under 35 U.S.C. §371 of International Application No. PCT/GB2009/001413, filed Jun. 5, 2009, which claims priority to the Great Britain Patent Application No. 0810445.7, filed Jun. 6, 2008.

The invention relates to an electrophoresis cassette, in particular, a pre-packaged electrophoresis cassette.

Gel electrophoresis is widely used in clinical and research laboratories apparatus for the separation and analysis of biological samples. In order to facilitate the process, pre-cast gel cassettes are available.

Pre-cast gel cassettes contain a separation gel, which has been formed so that it is ready for use. This gel will usually be either an agarose gel or a polyacrylamide gel. For electrophoresis to take place, an electric current must be passed through the gel via a buffer. Most pre-cast gel cassettes do not contain the necessary running buffer, and this is added before use. Where they do contain buffer, the buffer is usually contained in a gel. Although there is one known cassette in which the buffer is in the form of a solution, the sample is loaded directly into the gel, not onto the gel-buffer interface. The reason for this is that, over time, water is absorbed from the buffer solution into the gel, so causing a change in the gel structure, particularly at the gel-buffer interface. If the sample was loaded onto this gel-buffer interface, this change in the gel structure would interfere with the separation process.

It is an object of the present invention to seek to provide a pre-packaged electrophoresis cassette comprising a gel and a buffer solution, which has been optimised for, separation performance according to the sample to undergo electrophoresis, a good shelf life, and in which the sample can be loaded onto the gel-buffer interface.

Accordingly, the invention provides a pre-packaged electrophoresis cassette, the cassette comprising a gel layer and a buffer solution layer, the gel layer comprising a first polymer made from a monomer and a cross-linker, and being in contact with the buffer solution layer to form a gel-buffer interface for receiving a sample which is to undergo electrophoresis, the gel and/or the buffer solution being such that absorption of water by the gel layer from the buffer solution layer is inhibited.

The following test may be used to ascertain whether a particular gel and/or buffer combination inhibits absorption of water from the buffer solution into the gel.

The problem that is overcome is a change in gel structure/pore size over time. The gel is carefully optimised to give maximum resolution performance for the type of sample and size of sample the user wishes to separate. Adsorption of water into the gel alters the gel structure with adverse affects on the resolution performance. It is imperative, therefore, to stop changes in the gel structure such that there is no change in performance overtime.

Direct, detailed information on gel structure is difficult to obtain. Careful observation of the bulk gel and changes over time, such as observation of swelling, give a clear indication of a change in gel structure. Where possible, measuring any weight gain of a gel over time when in contact with aqueous solution gives an excellent measure of water adsorption and an implied change in gel structure (Park et al. Polymers for Advanced Technologies 2000, 617-625). More detailed techniques such as crystallography do not work because a gel by its nature is not in a crystalline state. There has been some attempt to use Environmental Scanning Electron Microscopy (ESEM) to study gel structure (Galaev et al. Soft Matter 2005, 303-309) but this technique can be time consuming for large varieties of gels. Alternatively Rheology has been used to estimate average gel pore size with results that are in surprisingly good agreement with corresponding data obtained from analysis of DNA electrophoretic mobility (Ugaz et al. Electrophoresis, 2006, 3349-3358). DNA electrophoretic mobility and electrophoretic separation performance is a standard measurement of pore size particularly (Solomon et al. Electrophoresis 2000, 3843-3850). Additionally, it has been reported that acrylamide/bisacryloylpiperazine (Bis PP) has a greater gel shear strength than acrylamide/methylenebisacrylamide (Bis AA) gels (Analytical Biochemistry, 173, 2, Sep. 1988, p. 412-423).

Together, the change in gel shape (swelling), weight gain, electrophoretic mobility, and electrophoretic separation performance over time give an excellent, reliable, and practical measure of change in gel structure. The applicant has applied these tests and found the most useful methods of measurement to be in situ of the device, i.e. electrophoretic mobility, electrophoretic separation performance and change in gel shape (swelling). The applicant has also applied weight gain and found this to be a useful ex situ method.

Using a 50 ml flat bottomed falcon tube 2 cm in diameter 10 ml of gel can be polymerised and 10 ml of buffer added on top. At periodic time intervals, the buffer solution can be decanted and the weight of the gel measured. The decanted solution can then be returned to the Falcon tube. An increase in weight demonstrates the uptake of water into the gel and indicates a necessary change in gel structure. In this test, a weight gain of more than 3 grams over 50 days demonstrates that the gel structure is not sufficiently stable to maintain separation performance.

Observation of the gel/buffer interface and changes with time can demonstrate swelling of the gel and a change in gel structure. In this test, a movement of the gel interface into the buffer solution of more than 10% of the width of the gel/buffer interface is considered to demonstrate that the gel structure is not sufficiently stable to maintain separation performance.

Separation performance of a gel can be expressed in resolution. Using chromatography principles resolution, R, can be calculated between two peaks by the ratio of the distance the two peaks are separated and the sum of the peak widths at half their peak height. In this test, a loss of more than 10% in resolution over 5 days is considered to demonstrate that the gel structure is not sufficiently stable.

The applicant has found that there are a number of different factors which affect absorption of water from the buffer solution into the gel.

The first factor is that there is a minimum concentration of monomer and cross-linker required to form a gel.

The concentration of monomer may be greater than 0.4M, preferably greater than 0.8M and more preferably greater than 1.0M.

The concentration of cross-linker may be greater than 4 mM, preferably greater than 6 mM and more preferably greater than 10 mM.

The second factor is the ratio of cross-linker to monomer used to make the gel. The applicant has found that, all other conditions being equal, absorption of water into the gel decreases as the ratio of cross-linker to monomer increases. Thus, the ratio of cross-linker to monomer in the gel may be such that absorption of water by the gel layer from the buffer solution layer is inhibited.

The ratio of cross-linker to monomer may be greater than $[4 \times 10^{-3}]$, preferably greater than $[6 \times 10^{-3}]$, more preferably greater than $[10 \times 10^{-3}]$.

The third factor is the rigidity of the gel structure. The applicant has found that, all other conditions being equal, absorption of water into the gel decreases as the rigidity of the gel structure increases. The rigidity of the gel structure is dependent on the cross-linker. Thus, the cross-linker may be such that absorption of water by the gel layer from the buffer solution layer is inhibited.

To function as a crosslinker a compound should contain at least two reactive groups. Suitable crosslinkers may have two C=C groups or two allyl groups and may be of the form:

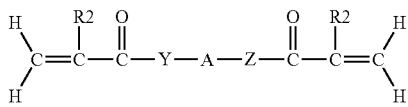

wherein R2 is either a hydrogen or a methyl group;
Y and Z are either NH groups or an oxygen; and
A is a non charged linker sequence which can be either hydrophobic or hydrophilic.

Acrylamide crosslinkers (where Y and Z are NH groups) include Bis AA, N,N'-ethylenebis(acrylamide), N,N-(1,2 dihydroxy-ethylene)bisacrylamide, N,N'-bis(acryloyl)cystamine, and Bis PP. Acrylate crosslinkers (where Y and Z are oxygen) include poly(ethyleneglycol)diacrylate (PEG), 1,4-butanediol diacrylate, 1,4-butanediol dimethacrylate. Suitable crosslinkers having more than two reactive groups include triacryloyl-hexahydrotriazine (TRI), which has three allyl groups, and tetraallyloxyethane and pentaerythritol tetraacrylate which have four allyl groups.

When selecting a cross-linker to improve the rigidity of the gel structure the following rules should be considered. The cross-linker should have as little flexibility as possible. For example a relatively small cross-linker such as Bis AA is considerably smaller and forms a more rigid gel than PEG cross linkers. PEG cross-linkers themselves form more rigid gels with less ethyleneglycol repeating units.

Cross-linkers should have as little rotation in the polymer chain as possible to increase rigidity of the gel. For example those that have single bonds in the chain allow rotation and increase flexibility. For example PEG cross-linkers can rotate around the C—O bond and Bis AA can rotate at the N—C—N bond. Bis PIP, however, and TRI have ring structures that don't allow rotation.

Cross-linkers should be able to bind into the monomer chain in more than one place. For example allyl polyvinylacetate only has one reactive double bond group available to bond with an acrylamide monomer chain. As a consequence the gel structure is very flexible. Bis AA bonds twice linking monomer chains and is considerably more rigid. TRI can bind three times to the monomer chain and can give a more rigid gel structure again. However, cross-linkers with more than three reactive double bond groups will not always be successful at binding to the monomer chain because of difficulties controlling the reaction and getting all reactive groups to cross-link.

Suitable monomers for use in the present invention include acrylamide, dimethylacrylamide, vinyl acetamides, 4-acryloylmorpholine, diacetone acrylamide, N-hydroxyethyl acrylamide, N-(1,1-dimethyl-3-oxobutyl)-acrylamide, N,N-dimethylacrylamide, N-[3-(dimethylamino)propyl]methacrylamide, N-isopropylacrylamide, N-tert-butylacrylamide, N-[tris-(hydroxymethyl)methyl] acrylamide.

The fourth factor is the hydrophilicity of the cross-linker. Hydrophilicity is generally judged according to how polar a compound is, which can be inferred by analysis of the chemical structure of a molecule and its polarity. However, while molecules can be described as "polar" or "non-polar", it should be noted that this is often a relative term, with one molecule simply being more polar or more non-polar than another. For example, N,N'-Diallyltartramide (DATD) has two hydroxyl groups whereas Bis AA, Bis PIP, and TRI have none. Accordingly, DATD forms a much less rigid gel structure.

These rules can be applied to other available cross-linkers. For example 1,3-Butanediol diacrylate has rotation around the C—O bond, and is larger than Bis AA. This cross-linker will therefore form a less rigid gel structure. 1,6-Hexanediol ethoxylate diacrylate is a long chain flexible polymer that has rotation around the C—O and C—C bonds and will form a relatively flexible gel structure.

The fifth factor is the chemical stability of the cross-linker itself. The applicant has found that PEG is susceptible to hydrolysis over time presumably at the ester group. To form a stable gel, the cross-linker must be chemically stable to hydrolysis.

In the context of the cross-linkers used in this invention, chemically stable to hydrolysis should be interpreted as the crosslinking bonds not breaking down in the presence of water. If the crosslinking bonds were to break down in the presence of water, the gel would become a liquid.

The sixth factor is the composition of the gel layer. The applicant has found that absorption of water by the gel layer from the buffer solution layer may be inhibited by the addition of a second polymer to the gel. Suitable polymers include non-charged polymers with an allyl group.

The second polymer may chemically bond to the first polymer in addition to the first cross-linker. The second polymer will then increase the entanglement of the first polymer, thereby decreasing its pore size, and so its tendency to absorb water. An example of a suitable second polymer is allyl agarose. Additionally, allyl polyvinyl-alcohol is a suitable second polymer. Allyl agarose will not only inhibit water absorption by copolymerising with the first polymer, but it will also inhibit water absorption because it is less hydrophilic.

The second polymer may form a mixed bed system where it can form a gel independent of the first polymer. The second polymer by forming a gel can add to the total gel strength. The second polymer may also be less hydrophilic than the first polymer. It will then have less tendency to absorb water than the first polymer and so will inhibit absorption of water by the gel layer from the buffer solution. Examples of suitable second polymers include D1 agarose, D5 agarose, MS4 Agarose (AGTC BioProducts Ltd) (AGTC BioProducts Limited, Hessle, UK), a high gel strength agarose with a very high molecular weight linear polymer chains.

The concentration of agarose may be between 0.1 and 3%, preferably between 0.3 and 1% and more preferably 0.4% by weight.

It may be preferable for the agarose to be a relatively low concentration so as to not affect the separation performance of the first polymer and only be a tool for inhibiting water adsorption. A high gel strength agarose is therefore preferred over a lower gel strength agarose.

The seventh factor is the electroosmotic difference between the gel layer and the buffer solution layer. The applicant has found that, all other conditions being equal, absorption of water into the gel decreases as the electroosmotic difference between the gel and the buffer solution decreases. Thus, the gel and/or the buffer solution may comprise means to reduce the electroosmotic difference between the gel layer and the buffer solution layer. An example of a suitable means for reducing the electroosmotic difference is an alcohol or ketone such as methanol.

Using these factors, it is possible to modify conventional gels and/or buffer solutions so that they inhibit water absorption by the gel layer from the buffer solution.

Any suitable gel and/or buffer solution may be used. For example, the gel may be an agarose or a polyacrylamide gel, and the buffer solution may be Tris-Acetate-EDTA (TAE), Tris-Borate-EDTA (TBE), Tris-Taurine-EDTA (TTE), Bis-Tris-Tricine (BTT), Tris-glycine-sodium dodecyl sulphate (SDS), Tris-Tricine-SDS, Bis-Tris-Tricine-lithium dodecyl sulphate (LDS), or 4-2-Hydroxyethyl morpholine/glycyl glycine/Histidine. Acrylamide gels are preferable to agarose gels as they exhibit greater chemical stability at the gel-buffer interface. Acrylamide gel is preferable to dimethacrylamide gel as it exhibits a lesser degree of swelling at the gel-buffer interface.

The gel can be optimised according to the type of sample to be separated. For example to separate an RNA sample the pore size of the gel should be relatively larger. The acrylamide concentration should therefore be low and the ratio of the cross-linker to monomer relatively low. Individually this polyacrylamide gel structure would not be stable when stored over time in contact with a buffer solution. It can be stabilised, however, by the use of agarose. In this way, the separation performance is maximised by the acrylamide gel and the gel itself stabilised by the agarose.

For DNA fragments (for example more than 1000 bp) agarose gels are typically preferred to polyacrylamide gels because agarose has larger pore sizes more suited to large DNA fragments. Equally a very low cross-linker to monomer ration can be selected to give a high porosity polyacrylamide gel but would have poor stability when stored with buffer over time. However this gel can be stabilised by the addition of allyl agarose.

For smaller DNA fragments (for example less than 1000 bp) and protein samples the concentration of monomer and cross-linker can be optimised for best separation performance and, by selecting a more rigid cross-linker such as Bis PIP, stabilised for good shelf-life when stored with buffer.

For protein fragments polyacrylamide gels are preferred. A detergent such as LDS or SDS may be used. Use of a detergent may lead to increased swelling, but a higher concentration of cross-linker may be used to counteract the swelling.

In use, the buffer solution layer may be located above the gel layer. This means that the sample may be readily loaded onto the gel-buffer interface by adding it to the buffer solution in a solution which is denser than the buffer solution so that the sample sinks to the gel-buffer interface.

The invention will now be illustrated by way of example with reference to the following drawings, of which:

FIGS. 7a and 7b show the gel layers of Example 5 before electrophoresis, together with plots showing the width and the resolution of the bands;

Figure 1A:
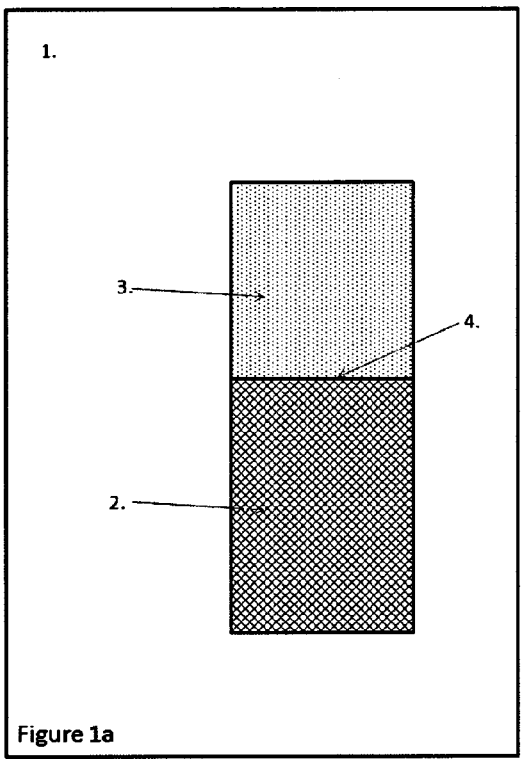
FIGS. 1a and 1b show schematic views of an electrophoresis cassette according to the invention, in use.

FIG. 1a shows an electrophoresis cassette 1. The electrophoresis cassette 1 contains a first layer of separation gel 2 and a second layer of running buffer solution 3, positioned above the layer of separation gel 2. The boundary between the two layers 2,3 forms a gel-buffer interface 4.

The separation gel 2 used in the cassette 1 may be based on any conventional separation gel. For example, it may be based on an agarose gel or a polyacrylamide gel. Similarly, the running buffer solution 3 used in the cassette 1 may be based on any conventional buffer solution. Where the gel 2 and/or buffer 3 differ from conventional gels/buffers is that they have been modified to inhibit absorption of water from the buffer 3 into the gel 2 as illustrated by the examples given below.

Figure 1B:
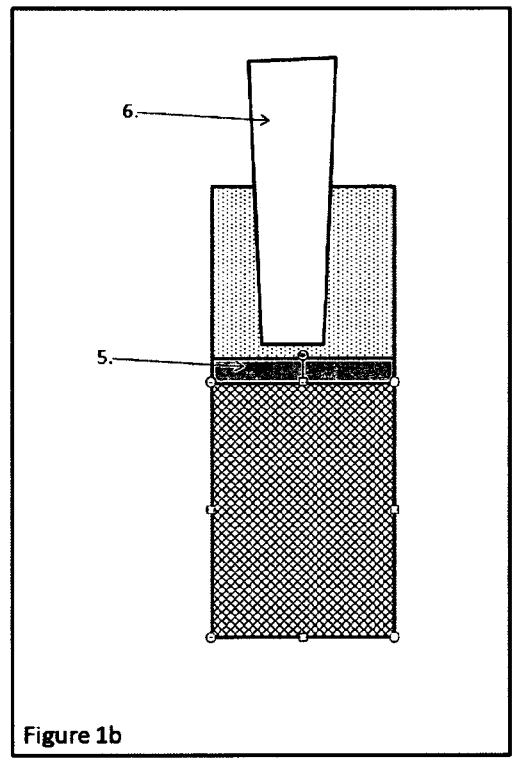

FIG. 1b shows a sample 5 which is to be separated being loaded onto the cassette of FIG. 1a. The sample 5 is added to the buffer solution 3 using a pipette 6. The sample 5 is in a solution which is more dense than the buffer solution 3. This means that it sinks to the top of the gel layer 2, that is, to the gel-buffer interface 4.

Once the sample 5 has been loaded onto the cassette 1, then conventional electrophoresis may be carried out.

EXAMPLE 1

10 ml of gel solution comprising a monomer and a cross-linker were polymerised in a 50 ml Falcon tube to form a gel layer. 10 ml of buffer solution was added on top of the gel layer to form a buffer solution layer. The monomer was acrylamide. The cross-linker was bis-acrylamide (Bis AA). The buffer solution was 50 mM Bis-Tris and 100 mM Tricine.

At periodic time intervals, the buffer solution was decanted and the weight of the gel was measured. The decanted solution was then returned to the Falcon tube. The process was repeated using different concentrations of monomer and/or cross-linker. The monomer was then replaced by a different monomer, and the process was repeated again using different concentrations of that monomer and the cross-linker. The different monomer was dimethylacrylamide (DMA).

Figure 2:
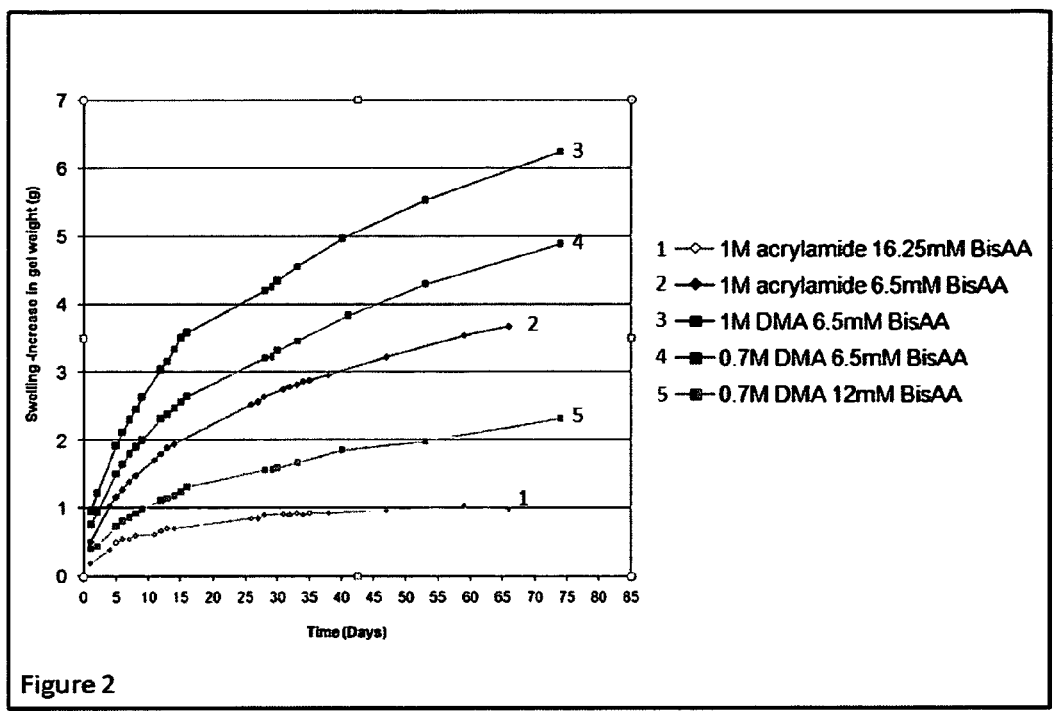
FIG. 2 shows a graph of swelling (increase in gel weight) vs time for Example 1.

The results are shown in FIG. 2 plotted as a graph of swelling (increase in gel weight) vs time. It can be seen that the amount of gel swelling which takes place over time decreases as the ratio of cross-linker:monomer increases, irrespective of whether the monomer is acrylamide or DMA.

EXAMPLE 2

A cassette was prepared by adding 1 ml of the cross-linker solution to 100 ml of the acrylamide/buffer solution to give a final solution of 1M acrylamide and 6.5 mM bis-acrylamide and the acrylamide was polymerized. The monomer was acrylamide. The cross-linker was bis-acrylamide (Bis AA). The buffer solution was 50 mM Bis-Tris, 100 mM Tricine. Electrophoresis was then carried out on the cassette.

Figure 3:
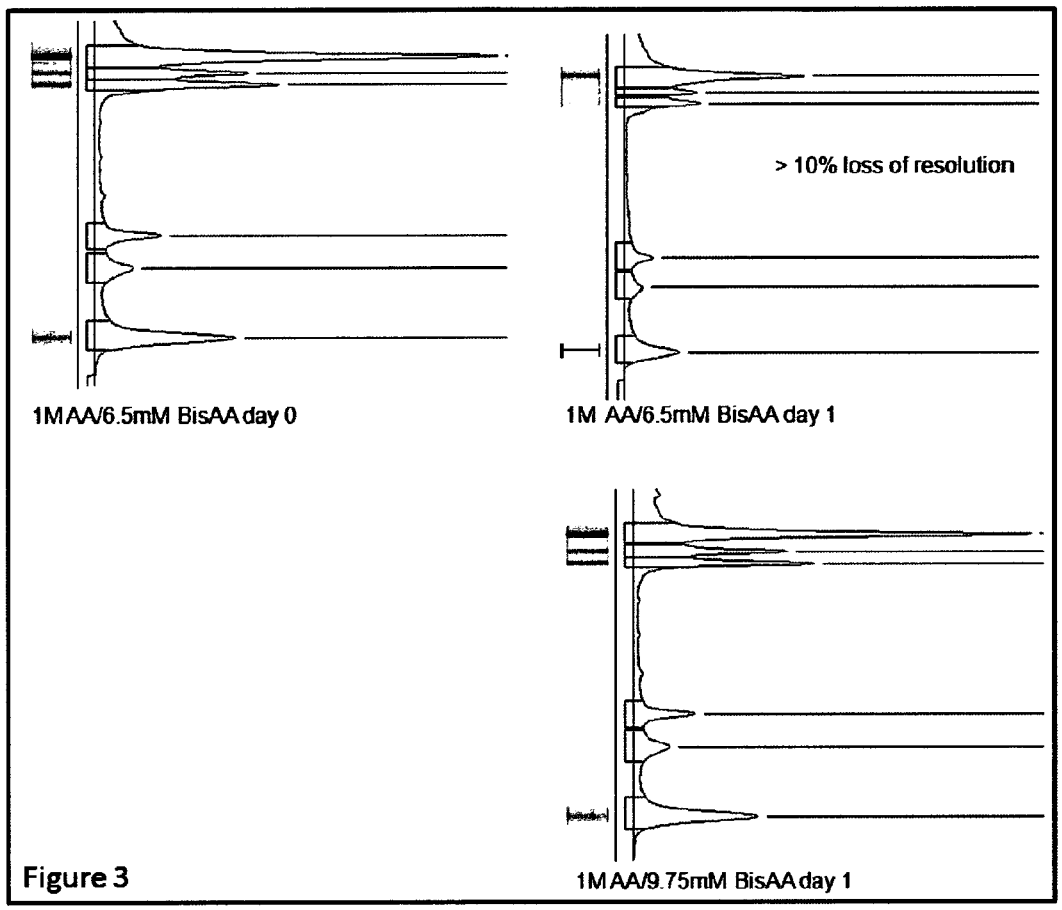
FIG. 3 shows the gel layers of Example 2 before electrophoresis, together with plots showing the width and the resolution of the bands.

The results are shown in FIG. 3. Each gel layer is shown before electrophoresis has taken place next to a plot showing the width and the resolution of the bands. It can be seen that, for the sample having the lower ratio of cross-linker to monomer, there is a significant loss of performance when the cassette is prepared 1 day before electrophoresis is carried out. This loss of performance can be seen in the broadening of the bands and more than 10% loss of resolution. No such loss of performance is seen for the sample having the higher ratio of cross-linker to monomer when the cassette is prepared 1 day before electrophoresis is carried out.

EXAMPLE 3

A cassette was prepared as in Example 2 using the same monomer and cross-linker. Electrophoresis was then carried out on the cassette.

The process was repeated varying the time interval between preparation of the cassette and carrying out electrophoresis, and using different concentrations of cross-linker.

Figure 4:
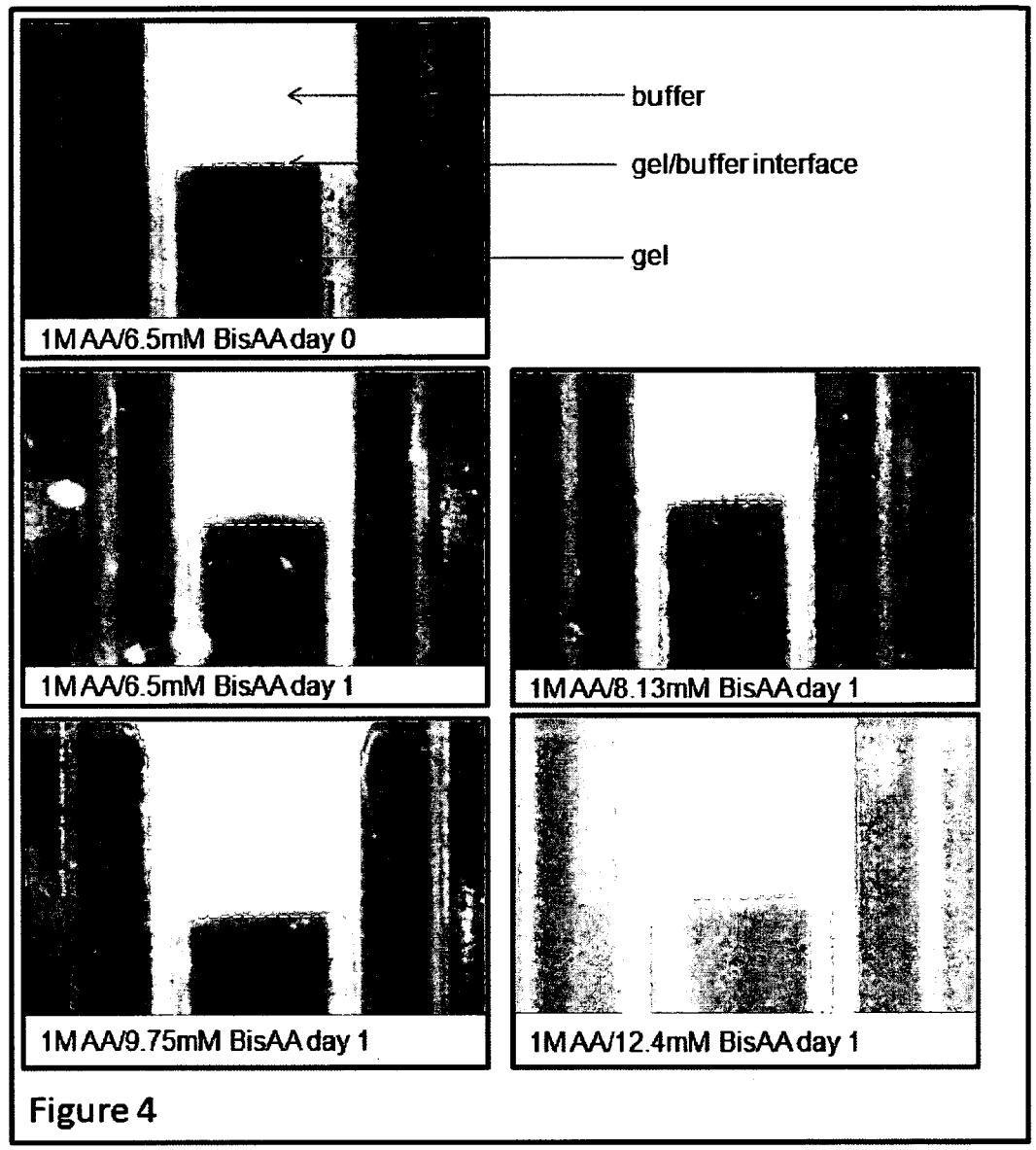
FIG. 4 shows the gel layers of Example 3.

The results are shown in FIG. 4. Each gel-buffer interface is shown before electrophoresis has taken place. It can be seen that, for the sample having the lowest ratio of cross-linker to monomer, there is visible swelling at the gel/buffer interface when the cassette is prepared 1 day before electrophoresis is carried out. For the samples having higher ratios of cross-linker to monomer, no such swelling is seen, and the gel maintains its structure even when the cassette is prepared 1 day before electrophoresis is carried out.

EXAMPLE 4

Example 1 was repeated using acrylamide as a monomer and a number of different cross-linkers. The different cross-linkers were poly-(ethyleneglycol)diacrylate (PEG), bis-acrylamide (Bis AA), bis(acryloyl)piperazine (bis PIP) and 1,3,5-triacryloylhexahydro-1-3-5-triazine (TRI). The structure of these cross-linkers can be seen in FIG. 5. The monomer was acrylamide.

Of these cross-linkers, PEG is a large cross-linker, which is flexible as there is rotation at the C—O bonds. Bis AA is considerably smaller and is more rigid, but there is still rotation at the N—C—N bond. Bis PIP is more rigid again because of the ring structure. TRI has the potential to give the most rigid gel structure because it is able to polymerise with the acrylamide monomer at three points.

Figure 5:
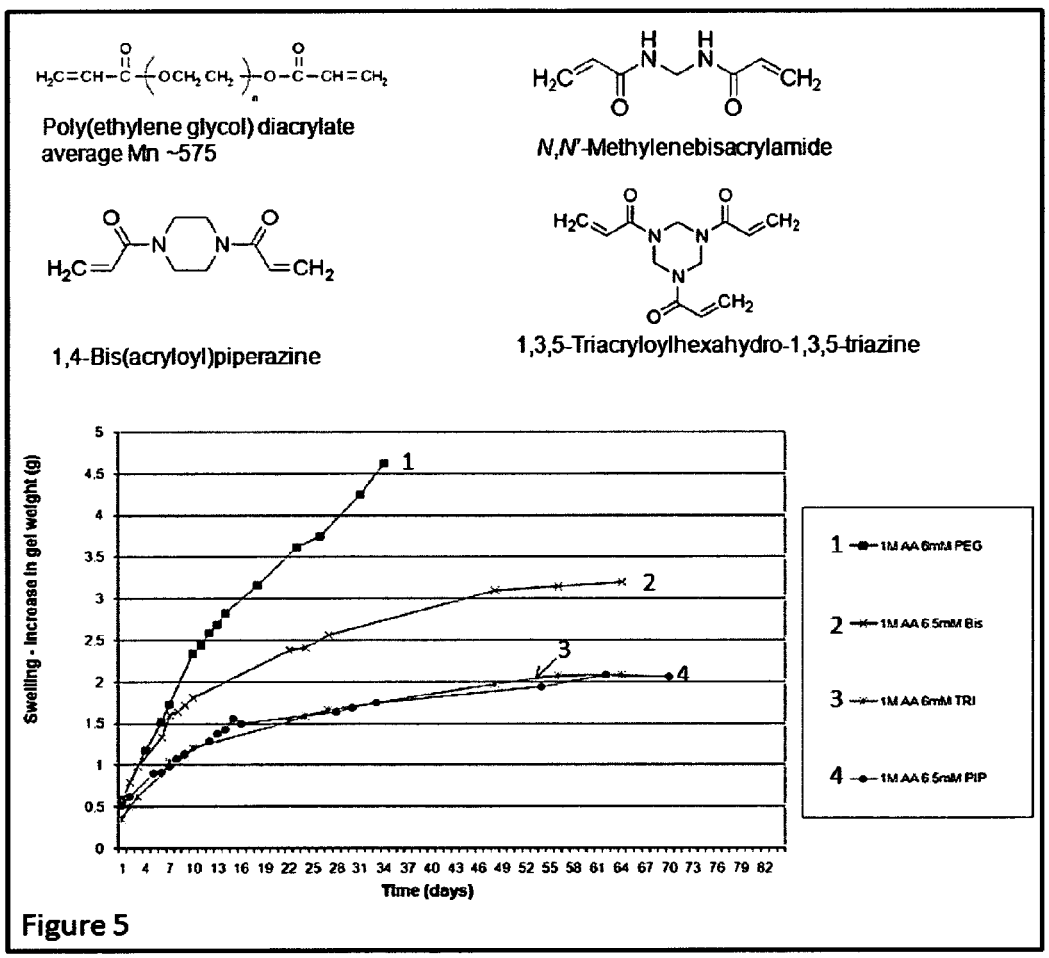
FIG. 5 shows a graph of swelling (increase in gel weight) vs time for Example 4.

The results are shown in FIG. 5 plotted as a graph of swelling (increase in gel weight) vs time. It can be seen that the amount of gel swelling which takes place over time decreases as the rigidity of the gel structure formed by the cross-linker increases.

Figure 6:
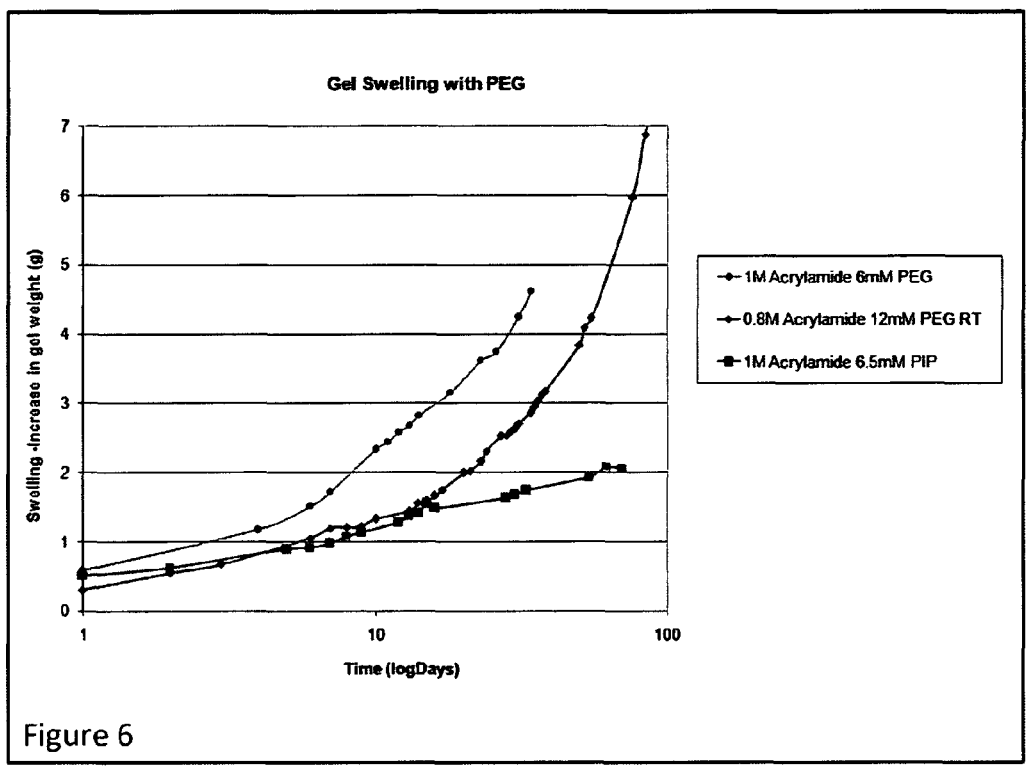
FIG. 6 shows a graph of swelling (increase in gel weight) vs time (log scale) for Example 4.

After 25 days the PEG cross-linker increases its rate of swelling. The increase in swelling rate is most likely due to chemical instability of PEG and cleavage of the ester group. When the concentration of PEG is increased to 12 mM the initial swelling due to hydration of the gel is controlled but the chemical instability is still present and after approximately 25 days the rate of swelling increases dramatically and eventually becomes a solution. FIG. 6 shows a graph of swelling (increase in weight) vs time (plotted as a log scale) for 6 mM and 12 mM PEG gels compared against 6.5 mM PIP.

EXAMPLE 5

Example 2 was repeated using acrylamide as a monomer and all the cross-linkers of Example 4 apart from bis-acrylamide (bis AA).

The results are shown in FIG. 7. Each gel layer is shown before electrophoresis has taken place next to a plot showing the width and the resolution of the bands. Each gel-buffer interface is also shown. It can be seen that, for a sample having 1M acrylamide and 6 mM PEG, there is a significant loss of performance when the cassette is prepared 14 days before electrophoresis is carried out. There is also considerable swelling at the gel-buffer interface. The gel interface has moved by more than 10%, resolution has decreased by more than 10% and DNA electrophoretic mobility has increased by more than 3%. However, a sample having 1M acrylamide and 6 mM PIP shows no loss of performance or swelling, even if the cassette is prepared 106 days before electrophoresis is carried out. Furthermore, a sample having 1M acrylamide and 4 mM TRI shows no loss of performance or swelling, when the cassette is prepared 21 days before electrophoresis is carried out, even though the ratio of cross-linker to monomer has been reduced. Thus, swelling at the gel-buffer interface over time, DNA electrophoretic mobility, and loss of performance increases as the rigidity of the gel structure formed by the cross-linker decreases.

However, the ratio of cross-linker to monomer can be used to compensate to some degree for a cross-linker of low rigidity. Thus, a sample having 0.8M acrylamide and 12 mM PEG shows no loss of performance or swelling when the cassette is prepared 7 days before electrophoresis is carried out. However, longer term, this performance cannot be maintained and the gel structure is broken down and solvated.

EXAMPLE 6

Example 2 was repeated using acrylamide as a monomer, bis AA as a cross-linker and a further monomer, allyl-agarose, which copolymerises with the acrylamide. The structure of allyl-agarose can be seen in FIG. 8.

Figure 8:
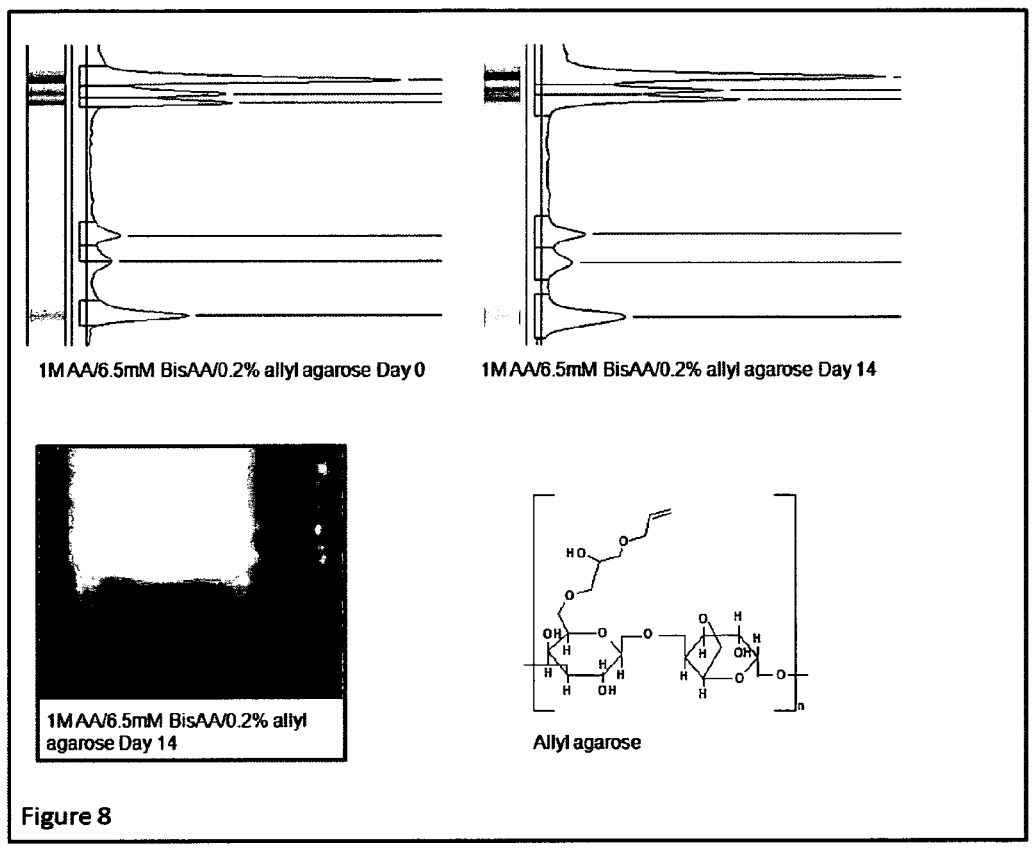
FIG. 8 shows the gel layers of Example 6 before electrophoresis, together with plots showing the width and the resolution of the bands.

The results are shown in FIG. 8. Each gel layer is shown before electrophoresis has taken place next to a plot showing the width and the resolution of the bands. Each gel-buffer interface is also shown. It can be seen that a sample having 1M acrylamide, 6.5 mM Bis AA and 0.2% allyl agarose shows no loss of performance or swelling when the cassette is prepared 14 days before electrophoresis is carried out.

EXAMPLE 7

Example 2 was repeated using acrylamide as a monomer, PIP as a cross-linker and a further monomer, D5 agarose (AGTC BioProducts Limited, Hessle, UK). D5 agarose is a high gel strength agarose with a very high molecular weight linear polymer chains. It does not copolymerise with the acrylamide.

The process was repeated with a standard agarose which has lower molecular weight linear polymer chains.

Figure 9:
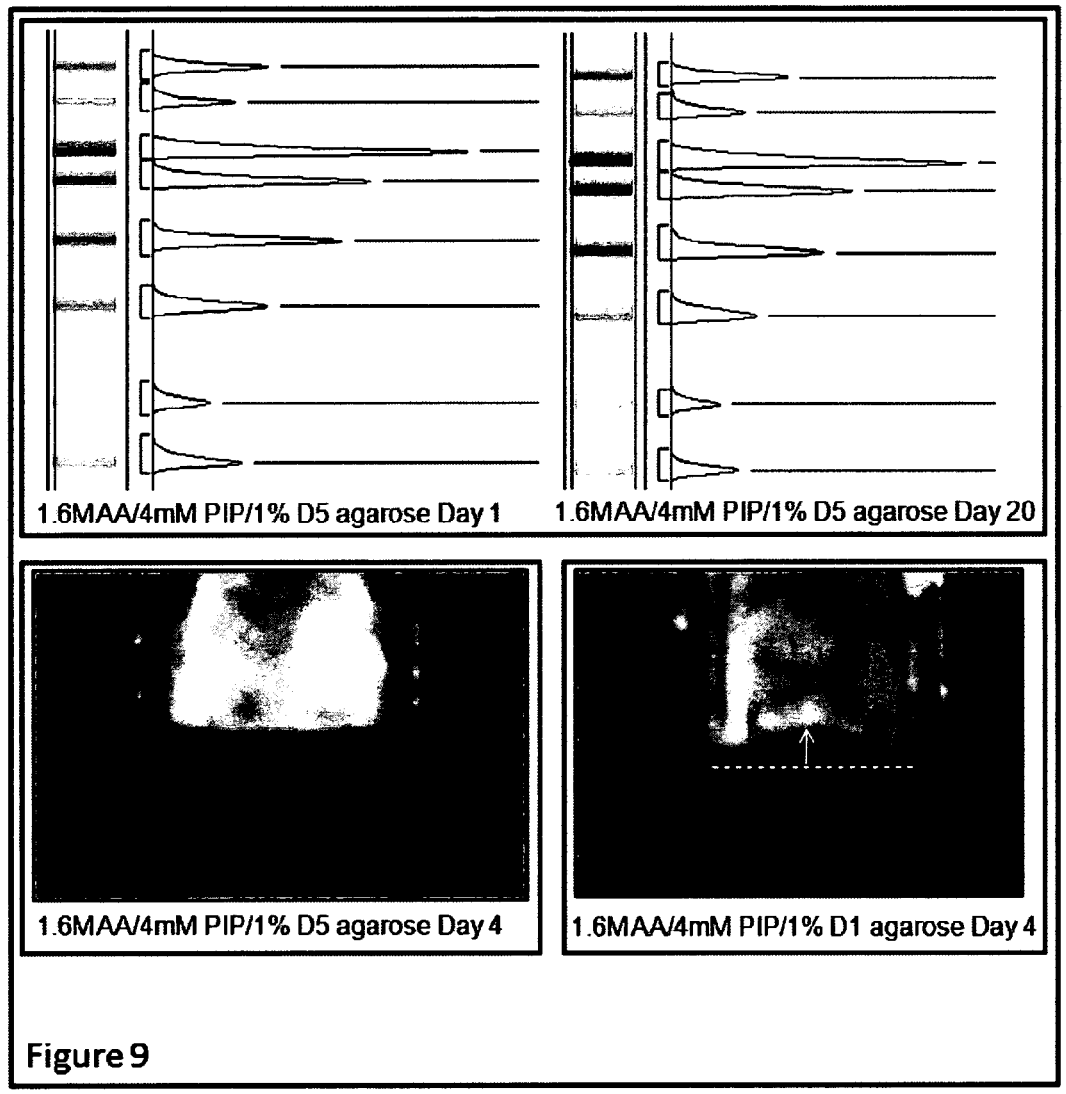
FIG. 9 shows the gel layers of Example 7 before electrophoresis, together with plots showing the width and the resolution of the bands.

The results are shown in FIG. 9. It can be seen that the sample which uses D5 agarose shows no loss of performance when the cassette is prepared 20 days before electrophoresis is carried out. However, when a sample using D5 agarose is compared with a sample using a standard agarose (D1, AGTC BioProducts Limited, Hessle, UK), the first sample shows no swelling when the cassette is prepared 4 days before electrophoresis is carried out, but the second sample shows considerable swelling over the same period.

The above examples are provided to illustrate the invention. Many possible variations will be apparent to the skilled person without departing from the scope of the claims.

EXAMPLE 8

Figure 10A:
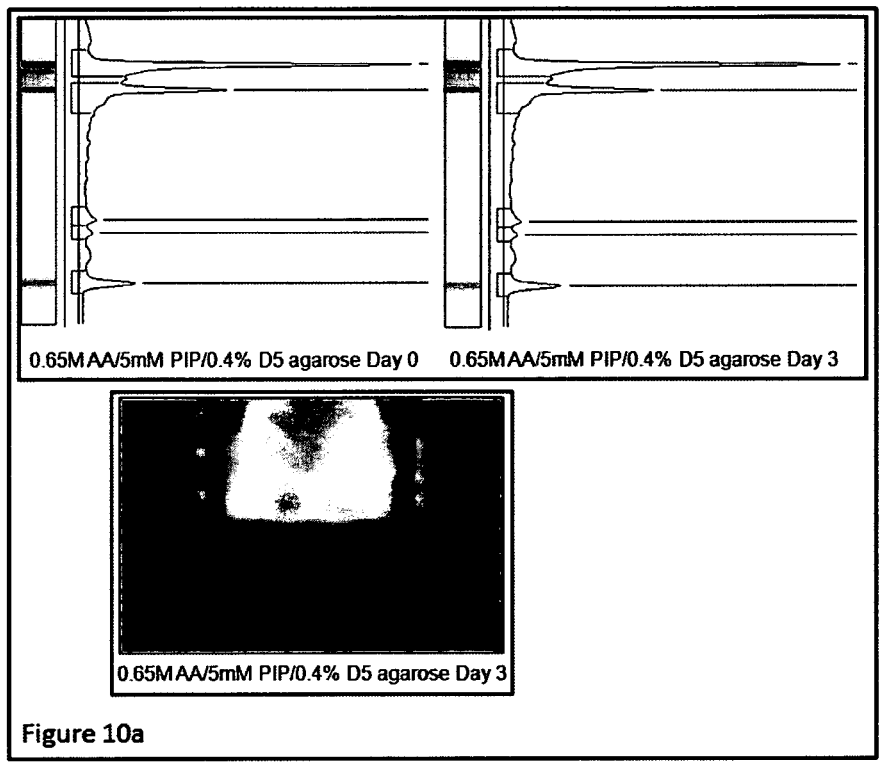
FIGS. 10a and 10b show the gel layers of Example 8 prepared 3 days before electrophoresis, together with plots showing the width and the resolution of the bands.
Figure 10B:
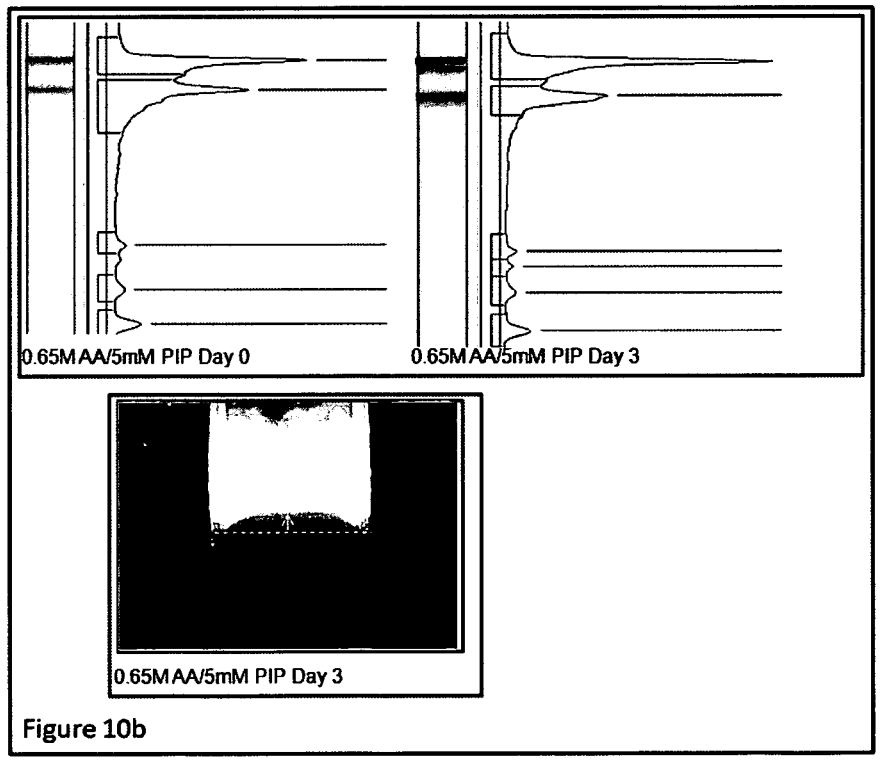

A gel has been optimised for the resolution of total RNA samples. The gel is prepared as 0.65 M acrylamide, 5 mM Bis PIP and 0.4% D5 agarose. Preferably the concentration of monomer would be higher, despite having a cross-linker to monomer ratio of $7.7 \times 10^{-3}$. Without the D5 agarose the gel swells and loses performance. FIG. 10 shows the gel together with buffer with and without D5 agarose prepared on the day of use and prepared 1 day before use and their separation performance.

EXAMPLE 9

Figure 11A:
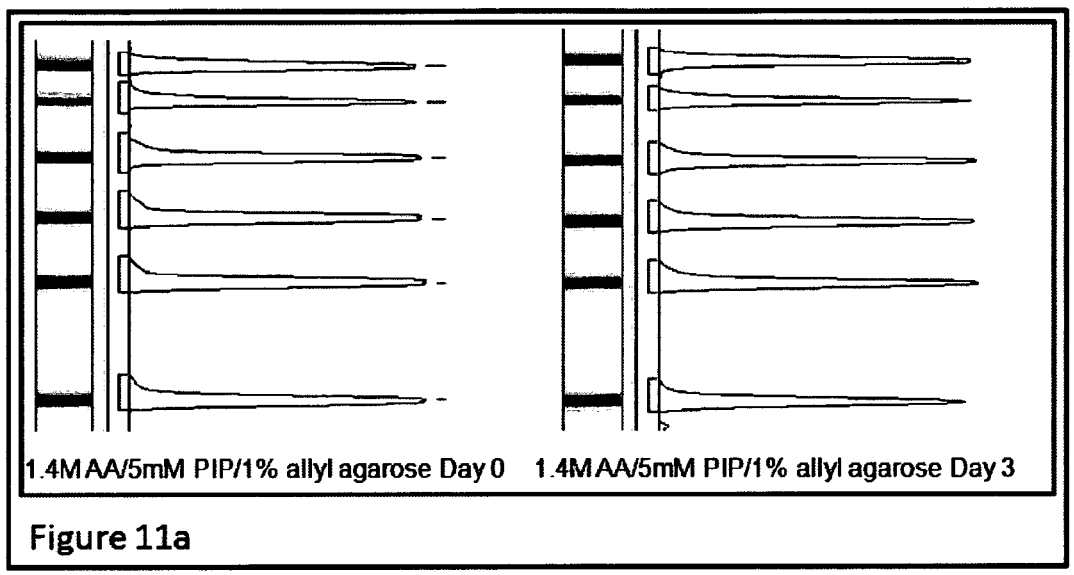
FIGS. 11a and 11b show plots of the width and the resolution of the bands of Example 9.
Figure 11B:
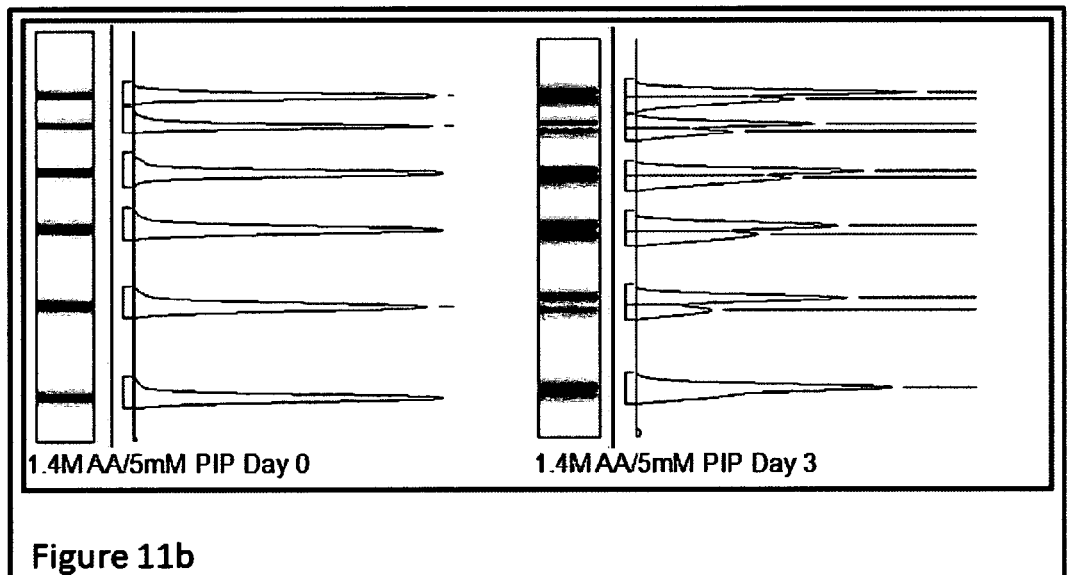

A gel has been optimised for the resolution of DNA fragments between 100 and 5000 bp. The gel is prepared as 1.4M acrylamide, 5 mM Bis PIP and 1% allyl agarose. The polyacrylamide gel has a cross-linker to monomer ratio of $3.6 \times 10^{-3}$ and, without the allyl agarose, swells when stored with buffer. When prepared with allyl agarose the gel structure is stabilised. FIG. 11 shows the gel together with buffer with and without allyl agarose prepared on the day of use and prepared 1 day before use and their separation performance.

EXAMPLE 10

Figure 7B:
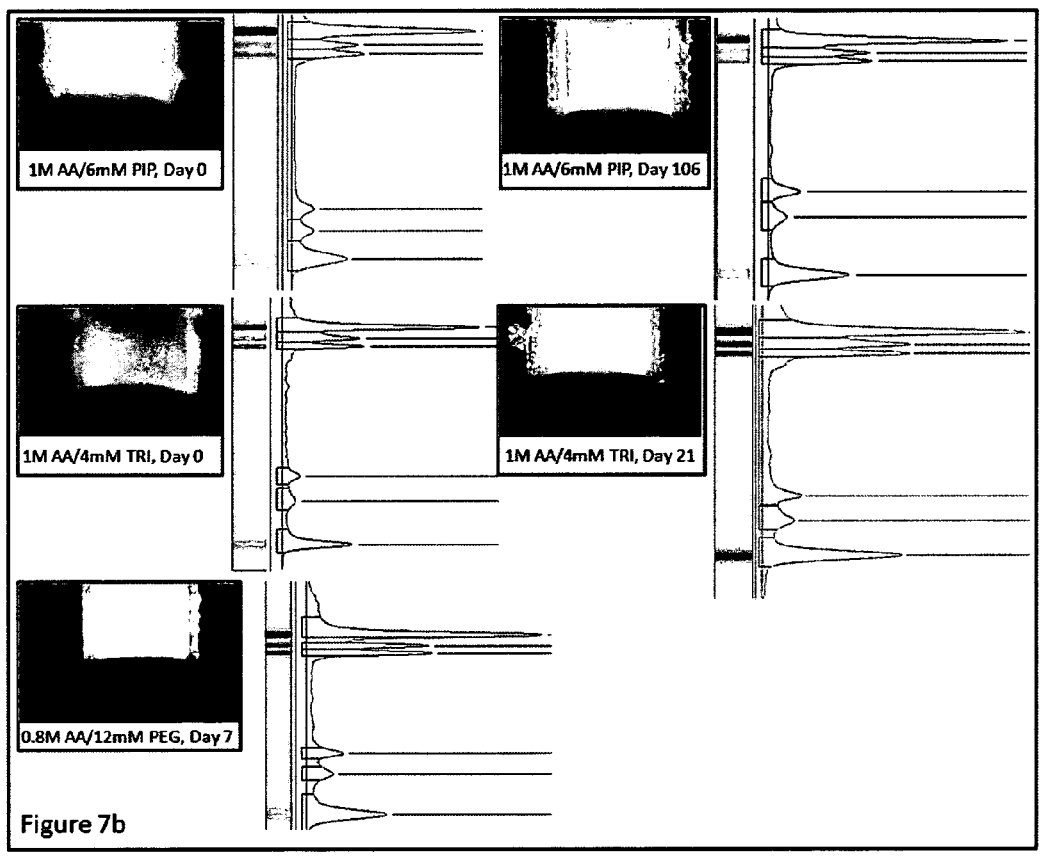

A gel has been optimised for the resolution of DNA fragments between 25 and 800 bp. The gel is prepared as 1M acrylamide, 6 mM Bis PIP. At this ratio of cross-linker to monomer using the traditionally favoured cross-linker Bis AA, the gel structure is not stable when stored with buffer over time (FIG. 3). However, by using Bis PIP the gel is stable (FIG. 7b).

EXAMPLE 11

Figure 12:
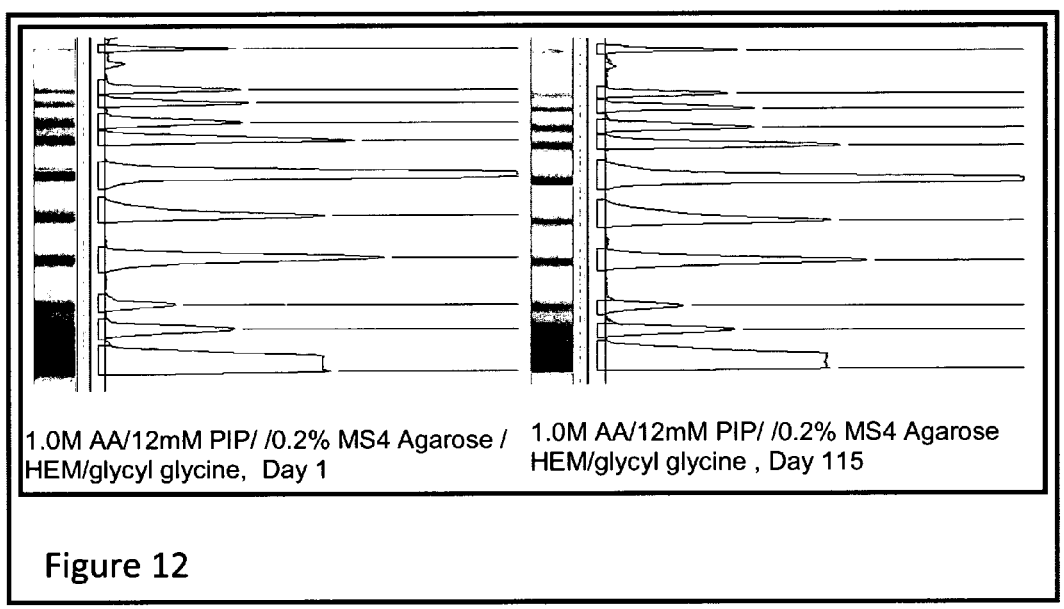
FIG. 12 shows plots of the width and the resolution of the bands of Example 11.

A gel has been optimised for the resolution of protein fragments (6 to 205 kDa in size). The gel is prepared as 1M acrylamide, 12 mM PIP, 0.2% MS4 Agarose (AGTC Bio-Products Ltd) in a buffer. At this ratio of cross-linker to monomer and using PIP, the gel structure is stable when stored with buffer over time (FIG. 12).

The invention claimed is:

1. A pre-packaged electrophoresis cassette, the cassette comprising a gel layer and a buffer solution layer, the gel layer comprising a first polymer made from a monomer and a cross-linker, and being in contact with the buffer solution layer to form a gel-buffer interface for receiving a sample which is to undergo electrophoresis, the gel and/or the buffer solution being such that absorption of water by the gel layer from the buffer solution layer is inhibited, wherein the cross-linker is selected from the group consisting of poly(ethyleneglycol)-diacrylate, methylenebisacrylamide, bis-(acryloyl)piperazine and triacryloyl-hexahydrotriazine.

2. The cassette according to claim 1, wherein the ratio of cross-linker to monomer in the gel is such that absorption of water by the gel layer from the buffer solution layer is inhibited.

3. The cassette according to claim 1, wherein the ratio of cross-linker to monomer is greater than [$4 \times 10^{-3}$].

4. The cassette according to claim 1, wherein the cross-linker is such that absorption of water by the gel layer from the buffer solution layer is inhibited.

5. The cassette according to claim 1, wherein the gel layer comprises a second polymer.

6. The cassette according to claim 5, wherein the second polymer is more hydrophobic than the first polymer.

7. The cassette according to claim 5, wherein the second polymer chemically bonds to the first polymer.

8. The cassette according to claim 1, wherein the gel and/or the buffer solution comprises means to reduce the electroosmotic difference between the gel layer and the buffer solution layer.

9. The cassette according to claim 1, wherein the first polymer is a polyacrylamide.

10. The cassette according to claim 1, wherein the buffer solution layer is, in use, located above the gel layer.

11. A pre-packaged electrophoresis cassette, the cassette comprising a gel layer and a buffer solution layer, the gel layer comprising a first polymer made from a monomer and a cross-linker, and being in contact with the buffer solution layer to form a gel-buffer interface for receiving a sample which is to undergo electrophoresis, wherein the monomer has a concentration greater than 0.4 M, the cross-linker has a concentration greater than 4 mM, and the ratio of cross-linker to monomer is greater than [$4 \times 10^{-3}$], the gel and/or the buffer solution being such that absorption of water by the gel layer from the buffer solution layer is inhibited.

12. The cassette according to claim 11, wherein the concentration of monomer is greater than 0.8 M or greater than 1.0 M.

13. The cassette according to claim 11, wherein the concentration of cross-linker is greater than 6 mM or greater than 10 mM.

14. The cassette according to claim 11, wherein the ratio of cross-linker to monomer is greater than [$6 \times 10^{-3}$] or greater than [$10 \times 10^{-3}$].

15. The cassette according to claim 11, wherein the cross-linker is selected from the group consisting of poly(ethyleneglycol)-diacrylate, methylenebisacrylamide, bis-(acryloyl)piperazine and triacryloyl-hexahydrotriazine.

16. The cassette according to claim 11, wherein the gel layer comprises a second polymer.

17. The cassette according to claim 16, wherein the second polymer is more hydrophobic than the first polymer.

18. The cassette according to claim 16, wherein the second polymer comprises a non-charged polymer with an allyl group.

19. The cassette according to claim 16, wherein the second polymer chemically bonds to the first polymer.

20. The cassette according to claim 11, wherein the gel and/or the buffer solution comprises a compound suitable for reducing the electroosmotic difference between the gel layer and the buffer solution layer.

21. The cassette according to claim 20, wherein the compound suitable for reducing the electroosmotic difference between the gel layer and the buffer solution layer comprises an alcohol or a ketone.

22. The cassette according to claim 11, wherein the first polymer is a polyacrylamide.

23. The cassette according to claim 11, wherein the buffer solution layer is, in use, located above the gel layer.

24. The cassette according to claim 11, wherein the cross-linker is selected from the group consisting of acrylamides, acrylates, and acrylic compounds having two or more reactive groups.

25. The cassette according to claim 11, wherein the cross-linker comprises two or more C=C groups or allyl groups.

* * * * *